US012702327B2

(12) United States Patent
Seifert et al.

(10) Patent No.: US 12,702,327 B2
(45) Date of Patent: Aug. 11, 2026

(54) METHOD FOR OPERATING AN ORTHOPEDIC DEVICE AND CORRESPONDING ORTHOPEDIC DEVICE

(71) Applicant: Otto Bock Healthcare Products GmbH, Vienna (AT)

(72) Inventors: Dirk Seifert, Vienna (AT); Michael Tschiedel, Vienna (AT); Robert Hoffmann, Vienna (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 1051 days.

(21) Appl. No.: 17/616,624

(22) PCT Filed: Jun. 5, 2020

(86) PCT No.: PCT/EP2020/065690
§ 371 (c)(1),
(2) Date: Dec. 3, 2021

(87) PCT Pub. No.: WO2020/245400
PCT Pub. Date: Dec. 10, 2020

(65) Prior Publication Data

US 2022/0225895 A1 Jul. 21, 2022

(30) Foreign Application Priority Data

Jun. 5, 2019 (DE) .................... 10 2019 115 096.5

(51) Int. Cl.
*A61B 5/11* (2006.01)
*A61F 2/64* (2006.01)
(Continued)

(52) U.S. Cl.
CPC ................ *A61B 5/112* (2013.01); *A61F 2/64* (2013.01); *A61F 2/70* (2013.01); *A61F 5/0102* (2013.01);
(Continued)

(58) Field of Classification Search
CPC ............................ A61N 1/36031; A61B 5/112
(Continued)

(56) References Cited

U.S. PATENT DOCUMENTS 5,831,937 A 11/1998 Weir et al.
10,137,025 B2 11/2018 Fior et al.
(Continued)

FOREIGN PATENT DOCUMENTS

CN 104394806 A 3/2015
CN 106821680 A 6/2017
(Continued)

OTHER PUBLICATIONS

China Patent Office "Office Action", issued in connection with China Patent Application No. 202080039870.3 dated May 23, 2024 (12 pages) (7 pages of English Translation and 5 pages Original Document).

(Continued)

*Primary Examiner* — Nadia A Mahmood
(74) *Attorney, Agent, or Firm* — HOLLAND & HART LLP

(57) ABSTRACT

The invention relates to a method for operating an orthopedic device which supports or replaces a first body part of a wearer and has at least one controllable actuator, wherein the method includes a) determining a chronological profile of at least one parameter, which allows for a conclusion to be made regarding a movement status of the wearer, from measurement values of at least one sensor; b) detecting the movement status from the at least one determined chronological profile; and c) controlling the at least one controllable actuator depending on the identified movement status, wherein at least the chronological profile of at least one parameter of a second body part of the wearer is also used to identify the movement status.

20 Claims, 6 Drawing Sheets

(51) Int. Cl.

| | |
|---|---|
| ***A61F 2/70*** | (2006.01) |
| ***A61F 5/01*** | (2006.01) |
| ***A61N 1/36*** | (2006.01) |
| *A61F 2/60* | (2006.01) |
| *A61F 2/68* | (2006.01) |

(52) U.S. Cl.

CPC ..... *A61N 1/36003* (2013.01); *A61N 1/36031* (2017.08); *A61B 2505/09* (2013.01); *A61F 2002/607* (2013.01); *A61F 2002/608* (2013.01); *A61F 2002/6818* (2013.01); *A61F 2002/6827* (2013.01); *A61F 2002/701* (2013.01)

(58) Field of Classification Search

USPC ............................................................ 607/49

See application file for complete search history.

(56) References Cited

U.S. PATENT DOCUMENTS

| | | | |
|---|---|---|---|
| 11,113,515 | B2 | 9/2021 | Matsuzawa |
| 2007/0050044 | A1 | 3/2007 | Haynes et al. |
| 2009/0043357 | A1 | 2/2009 | Tong et al. |
| 2013/0237884 | A1 | 9/2013 | Kazerooni et al. |
| 2014/0012164 | A1 | 1/2014 | Tanaka |
| 2015/0190248 | A1 | 7/2015 | Vitiello et al. |
| 2017/0119550 | A1 | 5/2017 | Sankai |
| 2017/0216075 | A1 | 8/2017 | Matsuzaki |
| 2018/0042654 | A1 | 2/2018 | Ingvarsson et al. |
| 2018/0147074 | A1 | 5/2018 | Battlogg |
| 2018/0311054 | A1 | 11/2018 | Schroeder |

FOREIGN PATENT DOCUMENTS

| | | | |
|---|---|---|---|
| CN | 109562265 | A | 4/2019 |
| DE | 4119150 | A1 | 12/1992 |
| DE | 102014117663 | A1 | 6/2016 |
| DE | 10 2016 114 075 | B3 | 11/2017 |
| EP | 2616115 | A1 | 7/2013 |
| EP | 2863846 | A1 | 4/2015 |
| EP | 3156010 | A1 | 4/2017 |
| JP | 2012-135486 | A | 7/2012 |
| JP | 2014-027978 | A | 2/2014 |
| JP | 6168488 | B2 | 7/2017 |
| JP | 2017205213 | A | 11/2017 |
| WO | WO 2012/037555 | A1 | 3/2012 |
| WO | WO 2013/190495 | A1 | 12/2013 |

OTHER PUBLICATIONS

International Search Report and Written Opinion issued in PCT/EP2020/065690, Dec. 10, 2020, 3 pgs.

"International Search Report and Written Opinion of the International Searching Authority," issued in connection with Int'l Appl. No. PCT/EP2020/06587, dated Sep. 25, 2020 (10 pages of English Translation and 13 pages Original Document).

Meyns Pieter et al. "The how and why of arm swing during human walking" GAIT & Posture, Elsevier, Amsterdam, NL, vol. 38, No. 4, Mar. 13, 2013 (Mar. 13, 2013), pp. 555-562 DOI: 10.1016/J.GAITPOST.2013.02.006 ISSN: 0966-6362, XP028733473.

METHOD FOR OPERATING AN ORTHOPEDIC DEVICE AND CORRESPONDING ORTHOPEDIC DEVICE

CROSS-REFERENCE TO RELATED APPLICATIONS

This is a national phase application of International Application No. PCT/EP2020/065690, filed 5 Jun. 2020, which claims the benefit of German Patent Application No. 10 2019 115 096.5, filed 5 Jun. 2019, the disclosures of which are incorporated herein, in their entireties, by this reference.

TECHNICAL FIELD

The invention relates to a method for operating an orthopedic device that supports or replaces a first body part of a wearer and comprises at least one controllable actuator, wherein the method features the following steps:

a) determining a chronological profile of at least one parameter, which allows for a conclusion to be drawn about a movement status of the wearer, from measurement values of at least one sensor, b) detecting the movement status from the at least one determined chronological profile, and c) controlling the at least one controllable actuator depending on the detected movement status.

BACKGROUND

In particular, orthopedic devices are prostheses and orthoses that are produced for limbs, i.e. arms and/or legs, of a wearer. An orthopedic device is usually arranged on a single limb, i.e. a single leg or a single arm, of the wearer. If the orthopedic device is a prosthesis, it replaces at least one body part. For example, this may be a foot, an ankle or a knee, but also a lower arm or a hand. Of course, there are also prostheses that replace multiple body parts. For example, a prosthesis produced for an upper leg amputee is designed to replace the knee, the ankle and the foot.

An orthosis, however, supports the respective body part. On the one hand, this comprises the support and protection against excessive strain, for example in a postoperative healing process by limiting an angular range in which a joint is to be used, for example, by means of an orthosis. Support within the scope of the present invention also includes support by relieving strain, which is achieved, for example, in sports orthoses or also in so-called exoskeletons, i.e. portable mechanical structures equipped with actuators if required, which are used in the medical field, for example, in rehabilitation or as an alternative to wheelchairs. There does not necessarily have to be a limitation of the user. For example, the use of such an orthosis/exoskeleton is also possible to reduce the strain on the body during physical activities, to increase performance and/or to reduce the risk of injury.

In particular, if the first body part is a leg or the amputation stump of a leg, it is important and of considerable advantage to know the movement status of the wearer in order to adapt the controllable actuator accordingly. Detectable movement statuses include, for instance, climbing and descending stairs, walking on a ramp, walking and running at different speeds, standing, sitting, climbing over obstacles that are in one's way, or a movement characteristic of a routine task. All of these different movement statuses often require different controls of the controllable actuator.

It is important to differentiate between a movement status of the wearer of an orthopedic device described above and the movement status or the movement of the respective body part. For example, when walking on level ground, the movement status of the wearer of the orthopedic device does not change as long as walking on level ground continues. However, the movement of the body part, for example a knee, changes multiple times during each step. It goes through standing phases and swing phases with different key moments, such as the heel strike. The detection and prediction of these key moments is also important for the control of an orthopedic device and has been known from the prior art for many years. In the scope of the invention described here, however, the detection of the movement status of the wearer of the orthopedic device is the primary focus as well as the question of how a change in movement status can be detected and the control of the orthopedic device adapted accordingly.

Consequently, the movement status of a wearer usually lasts for several step cycles, while the movement status of a body part changes on a much shorter time scale. This change can happen multiple times within a single step cycle. The at least one controllable actuator is preferably provided and configured to change the movement status of a body part, namely the first body part that is supported or replaced by the orthopedic device. In principle, it is not configured to change the movement status of the wearer of the orthopedic device.

With a controllable actuator, it may be, for example, a damping element, such as a hydraulic damper. In the case of hydraulic dampers, valves in particular are present in a fluid connection which can preferably be opened or closed in an infinite manner. The cross-section of the fluid connection is thus increased or decreased, by which the resistance against a flow of fluid and thus the damping caused by the damping element can be reduced or increased.

The controllable actuator may be a final control element by way of which a certain movement of at least one part of the orthopedic device or the entire orthopedic device can be controlled. For example, in the case of active orthopedic devices, such as active knee joints or active ankle joints, this is necessary so that the joint of the orthopedic device performs the desired function. Controllable actuators can be designed to be active or passive, regardless of whether they are damping elements or final control elements.

Means and methods for stimulating the musculoskeletal system, in particular electrostimulation of muscles and nerves, for example by means of electrodes, are also considered to be controllable actuators within the meaning of the present invention. These can be arranged, for example, on the wearer's skin and stimulate muscles below the skin via electrical impulses. They may also be subcutaneous electrodes, for example electrodes that lie on the nerve.

It has been known from the prior art for many years to control the controllable actuator depending on the detected movement status. To this end, the at least one sensor is configured to record measurement values from which at least one parameter can be determined, the chronological profile of which allows for conclusions to be drawn about a movement status. In this case, the chronological profile need not be detected or evaluated and documented across an entire step cycle. For example, the parameter may be the knee angle of a knee prosthesis or knee orthosis that is measured, for instance, across a step cycle and evaluated in the electric control system. The maximum knee angle differs depending on the movement status. The maximum angle of flexion that occurs, for example, with a knee is considerably greater when the wearer of the orthopedic device climbs stairs than when they walk on level ground. A conclusion about the movement status can be drawn from this, this information then being used to control the controllable actuator, for example, during the swing phase of the leg in such a way that the knee performs the desired movement.

Elsewhere, for example, it is useful to bring the foot into dorsal flexion, i.e. to raise the toes, when climbing stairs in the swing phase of the ipsilateral limb. This significantly reduces the risk of tripping and allows stairs to be climbed more smoothly and in line with natural movement.

The limb that is fitted and treated with the orthopedic device is referred to as an ipsilateral limb. Conversely, a limb that is not equipped with the orthopedic device is referred to as a contralateral limb. The contralateral limb may correspond to the ipsilateral limb if both limbs are arms or legs, for example. However, an arm that is not treated with the orthopedic device is also referred to as contralateral if the ipsilateral limb is a leg and vice-versa. Within the meaning of the present invention, this preferably also applies if both are on the same side of the body, i.e. a left arm and a left leg, or a right arm and a right leg.

Measurement values are usually recorded via the at least one sensor, from which parameters of the ipsilateral limb can be determined. For example, the knee angle, the ankle angle, various moments, relative positions of various components to each other, or speeds, accelerations or displacements of certain points of the orthopedic device relative to each other or in absolute terms can be determined. All of these parameters can be used to detect the movement status. However, it is a disadvantage that the movement status can only be detected once the measurement values have been captured, i.e. after or during the respective step. The determination of the movement status can therefore only be done retroactively. In this case, a control of the controllable actuator depending on the detected movement status is always based on the condition that the movement status of the wearer does not change between the two steps. The detected movement status in a step cycle is also deemed applicable for the next step cycle. Disadvantages arise if this is not the case and the movement status changes. This means that wearers of orthopedic devices, such as knee and lower leg prostheses, always start climbing stairs with the contralateral limb. This has the partial consequence that wearers who want to climb stairs have to change their stance leg before the stairs in order to start climbing stairs with the correct foot for them, i.e. the contralateral limb. This is inconvenient and uncomfortable, and also means that a wearer of an orthopedic device can be very easily recognized. As such, the intended illusion of natural movement is difficult or impossible to maintain.

SUMMARY

The present invention therefore aims to further develop a method for operating an orthopedic device in such a way that the detection of the movement status is improved and the movement performed by the wearer of the orthopedic device with the orthopedic device resembles natural movement as closely as possible.

The invention solves the problem by way of a method for operating an orthopedic device according to the preamble of claim 1, which is characterized in that, to detect the movement status, the chronological profile of at least one parameter of the second body part of the wearer is also used.

The invention is based on the knowledge that in particular the human gait, but also many other human movements, are fundamentally determined by the coordinated movement of various body parts, particularly two limbs. For example, to carry out a step, the stance leg must assume the movement of the body's centre of gravity and generate the forwards progression, while the swing leg must conduct the positioning of the foot in such a way that balance is maintained and an efficient transfer of weight enabled. If, for instance, a hand prosthesis is used to grasp a railing and support oneself on it, this also results in movements of the shoulder and possibly the rib cage. The invention takes advantage of the idea of exploiting the correlations of such coupling to reconstruct and control the movement of the constrained ipsilateral limb at least also from a contralateral movement of the limb. This applies particularly, if not exclusively, to the intention, i.e. the detection of the movement status at the earliest possible point in time.

The at least one actuator of the orthosis can be controlled, for example, in such a way that the movement and/or support of the treated limb, which constitutes the first body part in this case, occurs depending on the movement of a contralateral limb, which in this case constitutes the second body part. For example, in an arm orthosis, the at least one sensor can detect a leg extension from a flexed position, which indicates a lifting motion. The orthosis is then actuated in such a way that the orthosis supports and/or performs a raising of the arms and/or an extension motion. However, it is also possible that the orthosis supports the lumbar spine, which constitutes the first body part and whose flexibility can be adjusted by an actuator. For example, the flexibility is altered when an extension motion of the legs from a flexed position and/or a flexing of the elbows from an extended position is detected, especially when the upper body is leaning forwards. In both cases, the control of the actuator is coupled to at least a second body part.

According to the invention, the chronological profile of a parameter is used to detect the movement status. An individual measurement that provides a measurement value at a single point in time is not enough. It is beneficial, but not necessary, for the chronological profile of the parameter to be determined across one or especially preferably multiple cycles, such as step cycles, particularly in the case of repetitive movements. This is usually done by taking a plurality, preferably a large number, of individual measurements, each of which provides the measurement value at a single point in time. The results of the individual measurements are stored and evaluated as a chronological profile. The plurality of individual measurements may be taken equidistantly in terms of time. The interval between two individual measurements must be small compared to the length of, for example, a step cycle, so that a chronological profile of the parameter can be detected from the plurality of individual measurements.

It is often advantageous and sufficient to determine the chronological profile of the parameter not across entire step cycles, but, for example, only across certain sections of a step cycle. To detect a movement status, it is often enough to know the parameter at very specific points in time of a step cycle, for example. These specific points in time may be, for example, when the heel hits the ground or when the toes come off. To calculate this point in time as precisely as possible, it is necessary or at least advantageous to measure and determine the chronological profile of the parameter in a particular time period before and after this specific point in time. This also falls under the definition of a chronological profile according to the invention.

If the wearer's movement status, i.e. particularly the type of movement, is detected, the controllable actuator can be controlled correspondingly. Preferably, it is not simple routines and chronological profiles stored in a data memory of an electronic control unit for certain movement statuses that are executed. Rather, the chronological profile of the parameter of the second body part is preferably used to control the at least one controllable actuator. As a result, the body part that is supported or replaced by the orthopedic device is moved harmoniously, naturally and in a manner that is adapted to the movements of the other body parts, especially the second body part, as optimally as possible. For example, a natural gait pattern is created by, for example, adapting the movement of an orthopedic device, such as a prosthetic socket, to the movement of a healthy leg, which in this case constitutes the second body part. Alternatively and additionally, the second body part may also be an arm whose natural swinging motion during walking or running is used to control the movement of a leg prosthesis or an orthosis.

With the method according to the invention, in particularly advantageous embodiments it is therefore possible to not only detect the wearer's movement status as early as possible and control the at least one controllable actuator accordingly, but also to adapt the movement of the actuator to the movement of various body parts, thereby increasing the wearer's acceptance of the orthopedic device.

Preferably, the first body part does not directly abut the second body part.

In a preferred embodiment, the at least one parameter is a relative position, relative movement and/or relative speed and/or relative acceleration and/or relative angle of the second body part to the first body part and/or of a first part of the second body part to a second part of the second body part. The second body part is preferably a foot, knee, upper leg, lower leg and/or a tendon in the leg. The second body part is preferably an untreated limb or a part thereof. However, it may also be beneficial for the second body part to be, for example, part of a limb on which the orthopedic device is arranged. For example, the second body part may be an upper leg or the amputation stump of a leg on which a prosthesis is arranged, the artificial knee or foot of which replaces the first body part, for example.

To determine the chronological profile of the relative movement, the position of the body parts in relation to each other and/or their position in an overall coordination system relative to at least one sensor are detected at multiple points in time, for example. Position is understood in particular to also mean the translational and/or rotational orientation in relation to each other.

Here, it is irrelevant whether the second body part, particularly the contralateral limb, is treated with another orthopedic device.

Of particular interest is the use of the tendon of an untreated leg as a second body part, said tendon representing the imaginary connecting line between a foot and a hip of the limb. The orientation and length of the leg tendon are particularly interesting measurement values, as well as their speeds and changes. On the one hand, the leg tendon provides information on the position of the foot of the contralateral limb in relation to the center of the body and the center of gravity. It therefore provides direct and indirect information on the progression and stability and/or foot positioning of the wearer. In addition, the movement of the leg tendon can be detected with conventional sensors, even if it is not usually used. The movement of the proximal endpoint of the leg tendon, i.e. the hip, can already be calculated via existing sensors, which can be integrated into an orthopedic device described here. Good assumptions can be made about the movement of the distal endpoint, i.e. the foot of the untreated limb, especially in the stance phase. During the swing phase, the movement, i.e. in particular the position and/or change in position, of the foot can be determined via the at least one sensor.

If the proximal endpoint and distal endpoint of the tendon of the untreated leg are known, it is possible, with the aid of, for example, known dimensions of the upper leg and lower leg of the wearer of the orthopedic device, to also determine a leg angle or knee angle that can be intuitively interpreted and used in control principles. The knee angle of the treated side is a proven control parameter.

Alternatively or additionally, in the case of a leg treated with the orthopedic device, i.e. the ipsilateral limb, the position of the contralateral, i.e. untreated, foot in relation to the ipsilateral foot can be determined. This may be done either exclusively within the sagittal plane or three-dimensionally. Once it can be assumed in many situations that at least one of the feet is in contact with the ground, a relative measurement of the distance between the ipsilateral foot and the contralateral foot can be considered a determination of an absolute trajectory. Direct position measurement is significantly more reliable than the twofold integration of acceleration measurements, not least because of the need for correct initial conditions during integration. Of course, it is also possible to determine accelerations and effective moments on a foot, and to represent them in the form of a measurement series or a chronological profile. The twofold integration over time gives the movement. The horizontal component of the foot movement provides information on the step length and therefore also the timing of a step. Of particular interest here is the moment when the contralateral foot passes the ipsilateral foot. This applies to both the stance and swing phase.

The relative positions of other points relative to each other, for example the ipsilateral knee axis to the contralateral foot, may also be of interest. The more sensors that are used, the more different parameters there are that are accessible for a measurement. Conclusions can also be drawn about other relative positions via kinematic chains, so that further parameters become accessible.

Conclusions can also be drawn about the segment angle of the contralateral side particularly from the relative positions and/or relative movements as well as the relative angles in various combinations. This affects, for example, the upper leg, the lower leg or the foot. From this, joint angles, such as the contralateral hip angle, knee angle or ankle angle can be determined.

By carefully selecting different sensors for determining different values, from which the various parameters, including those of the second body part, can be determined, conclusions can be drawn, for example, about the contralateral leg movement.

Preferably, the at least one sensor is configured to detect an absolute angle, a relative angle, a speed, an acceleration, a force, a pressure, a pressure wave, a moment, an electrical field and/or a magnetic field. A pressure wave is understood particularly to also mean a sonic wave, especially an ultrasonic wave.

The first body part is preferably an ipsilateral limb or a part thereof, particularly a foot, an ankle and/or a knee, and the second body part another limb, preferably a contralateral limb or a part thereof, preferably a foot, an ankle and/or a knee.

In a preferred embodiment, the at least one sensor is arranged on a component of the orthopedic device and/or on the first body part and preferably also detects at least measurement values from which the at least one parameter of the second body part, in particular of the contralateral limb, is determined. The at least one sensor is preferably a contactless sensor. In this case, there are different measuring principles to choose from. For example, the at least one sensor may determine information on the contralateral limb by measuring an influence of electrical, magnetic and/or electromagnetic or electrostatic fields. This applies, for example, by influencing oscillating circuits or by capacitive measurements. Such sensors are known from the prior art and familiar to experts, so that a more detailed description is not necessary.

Another operating principle of a contactless measurement is, for example, the determination of propagation times, reflections and interferences of waves that are preferably emitted by the sensor itself or another component arranged on the orthopedic device and/or the ipsilateral limb.

The at least one sensor is preferably arranged on the second body part, preferably the contralateral limb, and preferably at least also detects measurement values from which the at least one parameter of the functional body part, preferably the contralateral limb, is determined.

Advantageously, the at least one sensor therefore has at least one transmission device and at least one reception device. The transmission device emits measuring radiation, which is preferably ultrasonic waves or electromagnetic measuring radiation, such as radar radiation and/or visible light and/or infrared radiation. The reception device is configured to receive this measuring radiation. With such a sensor, the principles of interference measurement, triangulation and transit time measurement of different electromagnets or other measuring radiation are accessible. Suitable measuring radiations are electromagnetic waves in the radio and microwave range, for example radar, near and far infrared radiation and visible light, for example LIDAR. A corresponding reception device for visible light is, for example, a camera. If the measuring radiation is not electromagnetic radiation, ultrasound radiation may be used, for example. The measuring radiation emitted by the transmitter strikes the second body part, preferably the contralateral limb, and is influenced by it. On the one hand, this affects the reflection of the measuring radiation, but a change in frequency and in particular in the phases is also possible. The reception device is configured to receive this measuring radiation influenced by the second body part and to evaluate the information it contains.

Advantageously, the reception device is configured to receive measuring radiation reflected or re-emitted by the second body part, preferably the contralateral limb, and to determine the measurement values from a transit time, a phase shift, a frequency shift and/or interference with the emitted measuring radiation, and the at least one parameter from said values. The determination of the parameter and the evaluation of the measurement values is preferably not done in the reception device, but in the electric control system that is also used to control the controllable actuator.

These methods can also be used to detect orientations, distances, positions and, where applicable, speeds. In particular when determining the speed, the Doppler effect is used, for example. All of these methods and evaluation processes can be used in both the two-dimensional, such as the sagittal plane, and the three-dimensional. In addition, image recognition technologies that are known in principle from the prior art can be used to determine objects, especially the contralateral limb or parts of the contralateral limb.

Photogrammetry or light-section methods can also be used to extract, for example, depth-related information from the measurement values of the at least one sensor. All of these methods are preferably used in the electric control unit.

The measurement itself may be conducted at specific points, in a defined plane, or in a directional range, such as a transmission cone. It is possible to cover the entire scene in a single shot or to perform respective rasterizations. This can take advantage of the fact that the at least one sensor on the first body part or a component of the orthopedic device moves past the second body part, in particular the contralateral limb, or vice versa. The second body part is thus captured from different perspectives by the at least one sensor, thereby obtaining various information.

Transmitters and receivers are preferably mounted on the same body part, for example an ipsilateral or contralateral body part. In other embodiments it is also possible for transmitters and receivers to be located on different body parts. Furthermore, with multiple sensors, a combination of arrangements on both the same and a different body part is possible.

In a preferred embodiment, at least one transponder and/or a tag and/or a reflector for the emitted measuring radiation is arranged on the second body part, preferably the contralateral limb. This is a so-called target which, due to its geometric form and/or material properties, is easily identifiable for the corresponding sensor technology and electromagnetic radiation, and has clearly defined properties. Active and passive transponders can also be used, for example, to transmit identification information or independent measurement results as soon as they are hit by the measuring radiation. Such a transponder or target can be integrated, for example, in a band or strap arranged, for example, on the second body part or positioned in an item of clothing.

It has been proven advantageous for data of the orthopedic device and/or the wearer to be used for determining the at least one parameter, especially for determining the at least one parameter of the second body part, preferably the contralateral limb. Said data may be, for example, distances, possible swivel angles or length values. For example, to determine a knee angle of a contralateral leg from the leg tendon it is necessary to know, at least roughly, but preferably precisely, the lower leg length and upper leg length of the wearer of the orthopedic device on the contralateral side. Relative values of the contralateral side in relation to the ipsilateral side can also be converted into absolute values by measuring absolute measurement values on the ipsilateral side. For example, a contralateral lower leg angle corresponds to the ipsilateral lower leg angle plus the relative angle of the two lower legs.

During operation of the orthopedic device, one control variable of the at least one controllable actuator is preferably controlled to a set point or a set point profile. Advantageously, this not only depends on the detected movement status itself, but also on the parameters upon which this detection is based, particularly the at least one parameter of the second body part, preferably the contralateral limb.

The invention also solves the problem by way of an orthopedic device that supports or replaces a first body part, the orthopedic device having at least one sensor and an electric control unit that is configured to carry out a method described here.

When determining the at least one parameter of the contralateral limb, it is possible, as previously explained, to refer back to calculations of the corresponding parameter from sensor data. Alternatively or additionally, missing parameters that are not directly accessible with the used sensors can be determined from existing measurement values and, if applicable, a model or model assumptions. The existing measurement values can be measurement values of both the ipsilateral and contralateral side. Appropriate models are, for example, mechanical and kinematic models that describe the respective movements of the limb.

An example for an application of a method according to an example of an embodiment of the present invention proposes that the flexion resistance of a knee prosthesis or a cross-knee orthosis be reduced. The knee constitutes the first body part. This reduction or swing-phase release occurs in the ipsilateral stance phase depending on the leg angle and/or segment angle of the contralateral swing leg phase. It can also be done, at least in part, while walking down stairs and hills. The reduction is done in such a way that a reduction occurs when, or only when, the contralateral foot, i.e. the second body part, is sufficiently close to the ipsilateral foot, i.e. the foot on the first body part, or has already passed it in the anterior direction. Such a targeted reduction of flexion resistance makes it possible to make flexion resistance in the early stance phase higher than it is at present, or to prevent further flexion after a certain amount of knee flexion and only allow it again when the ipsilateral foot has swung sufficiently far forward. The timing of the reduction as well as the initial flexion resistance may also depend on the walking speed, with higher walking speeds leading to less excess flexion resistance and earlier reduction. For a prosthetic foot or cross-foot orthosis, the dorsal flexion movement and/or the resistance to dorsal flexion in the ipsilateral stance phase can be adjusted to allow for easy rollover. In particular, by swinging the contralateral side forward from a standing position, it can be detected that a forward step is initiated and dorsal flexion is allowed and/or initiated compared to standing, which facilitates rolling over the foot.

In another embodiment example, the trajectory of both the ipsilateral and contralateral foot in the respective swing phase is directly determined from the relative distance of the ipsilateral foot to the contralateral foot by way of the ground contact of the respective opposite side. The ipsilateral foot constitutes the first body part and the contralateral foot the second body part. In the case of a transtibial treatment or an ankle foot orthosis (AFO), this provides information on the height difference to be overcome. This can be both a positive height difference, i.e. one directed against the force of gravity, and a negative one, i.e. a downward climb. The aid is then controlled such that the foot optimally adjusts its inclination or stiffness to the situation before initial contact. In particular, when climbing downward, it is possible to bring the leading foot into greater plantar flexion in order to ascend with the forefoot at initial contact. It is also possible that during an upward climb of the contralateral side, the ipsilateral foot performs an active plantar flexion in its stance phase to raise the body's center of gravity and facilitate overcoming a height difference.

For cross-knee treatments, in addition to the relative position of the feet to each other, the relation of the movement of the swing leg and the stance leg can also be set in relation, especially the ipsilateral and contralateral leg tendons. In this case, multiple second body parts are used. The movement status, especially the overcoming of a height difference, can be calculated from the ratio of the movements. In particular during an upward limb with the ipsilateral side, the knee joint can be flexed to a more significant degree in the swing phase flexion and/or stopped in the flexed position at the end of the swing phase extension. This renders it easier to overcome a height difference. It is also possible for the knee prosthesis or cross-knee orthosis to be controlled in the swing phase in such a way that the movement of the ipsilateral foot is proportionate to the movement of the contalateral leg as well as the movement of the ipsilateral upper leg or upper leg stump. For example, the knee joint can be controlled in such a way that the step length of the leading ipsilateral foot corresponds approximately to that of the contralateral stance leg. For example, greater ipsilateral hip flexion with no change in contralateral leg movement may result in less knee extension or greater knee flexion.

In another example, the knee pre-flexion of a knee is adapted. If the knee joint is stopped while climbing ramps and steps as well as ascending at the end of the swing phase in a flexed position, the extent of the pre-flexion can be determined in such a way that the ipsilateral and contralateral leg angle are proportionate to each other during ipsilateral initial contact. The user therefore essentially determines the step length via the contralateral stance leg movement and the step height via the ipsilateral hip flexion or upper leg movement on the side that bears the aid.

A swing phase control is also possible. The flexion and extension resistances, i.e. the set points of an actuator, in the prosthesis-side swing phase could be set in such a way that the leg angle of the contralateral side in its stance phase and that of the ipsilateral side in the swing phase are proportionate to each other. The rolling movement of the contralateral side would thus determine the timing of the ipsilateral side, wherein the ipsilateral upper leg movement has a considerable influence on how the orthopedic device should engage in the movement.

In another example, the swing movement is detected. Some aids do not have any force sensors to determine whether the treated side is in contact with the ground. The contralateral leg movement can provide information on whether it is a backwards walking movement, during which the contralateral stance leg rolls backwards, or whether the stance leg is stationary and the ipsilateral side is being swung backwards under the body. In the latter case, with cross-knee treatments, a knee flexion can be permitted or initiated, which enables the climbing of steps or overcoming of obstacles. A similar approach can help to detect when the user moves the ipsiplateral side forwards, for example from standing.

An important application is the detection of tripping. Information on the contralateral leg movement can also indicate whether the user is tripping. This relates to tripping in both the ipsilateral and contralateral swing leg phase. Detection may be achieved through the abrupt stopping of an otherwise continuous movement on the one hand, or a too pronounced flagging of the swing leg side in relation to the rolling movement of the opposite side. The type of reaction when tripping is detected can also depend on where the opposite side currently is. Both a raising of the foot and/or an increase in ground clearance and a setting down of the foot and/or an increase in flexion resistance are possible.

When the relative distance of the contralateral and ipsilateral foot is measured, the step length is directly available and, in addition to control, can be used for activity tracking or assessment of gait symmetry. Walking speed can also be determined directly as distance traveled per time instead of estimating it from the rolling speed in the ipsilateral stance phase.

BRIEF DESCRIPTION OF THE DRAWINGS

In the following, some examples of embodiments will be explained in more detail by way of the attached figures: They show.

DETAILED DESCRIPTION

Figure 1:
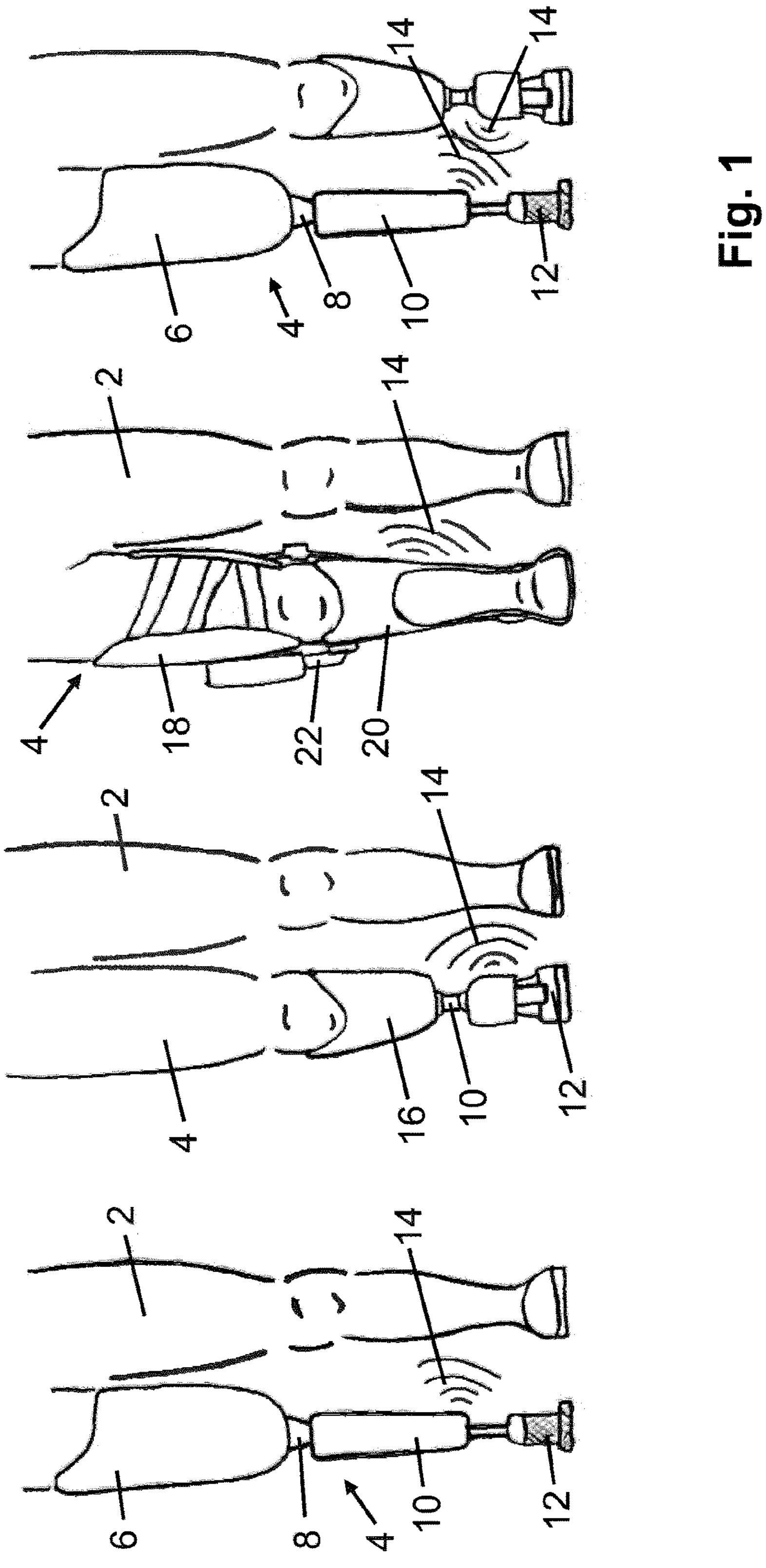
FIG. 1—four different orthopedic devices, each in a frontal view.

FIG. 1 shows, from left to right, four different treatment scenarios. At the far left, the legs of a wearer of an orthopedic device can be recognized, where the contralateral limb 2 is the left leg and he ipsilateral limb 4 is the right leg. In the far left representation in FIG. 1, a leg prosthesis with an upper leg socket 6, a knee joint 8, a lower leg 10 and a foot 12 is arranged on the ipsilateral limb 4. It is schematically shown that a sensor is located on the lower leg 10 which emits a measuring radiation 14 in the direction of the contralateral limb 2.

In the next representation, the contralateral limb 2 is again an untreated healthy leg, while a lower leg prosthesis is now arranged on the ipsilateral limb 4. It features a lower leg socket 16 to which the lower leg 10 and the foot 12 are attached. There is also a sensor arranged here which emits the measuring radiation 14 in the direction of the contralateral limb.

The third representation from the left shows a healthy contralateral limb 2 and a fully present ipsilateral limb 4 on which an orthopedic device in the form of an orthosis is arranged. It has an upper leg frame 18, a lower leg frame 20 and a knee joint 22, on which a controllable actuator is located. In this case too, the sensor is arranged in the lower leg area, i.e. on the lower leg frame 20, said sensor emitting the measuring radiation 14 in the direction of the contralateral limb.

The far-right representation of FIG. 1 depicts the ipsilateral limb 4 as it is shown in the far-left representation. However, unlike in the far-left representation, the contralateral limb is also treated with an orthopedic device, namely a lower leg prosthesis corresponding to the orthopedic device shown in the second representation from the left. Both orthopedic devices now have one sensor that emits measuring radiation 14 in the direction of the respective other limb. In the case of the orthopedic device depicted on the left in FIG. 1, i.e. on the right leg, the opposite side refers to the contralateral limb, even if it is treated with an additional orthopedic device.

Figure 2:
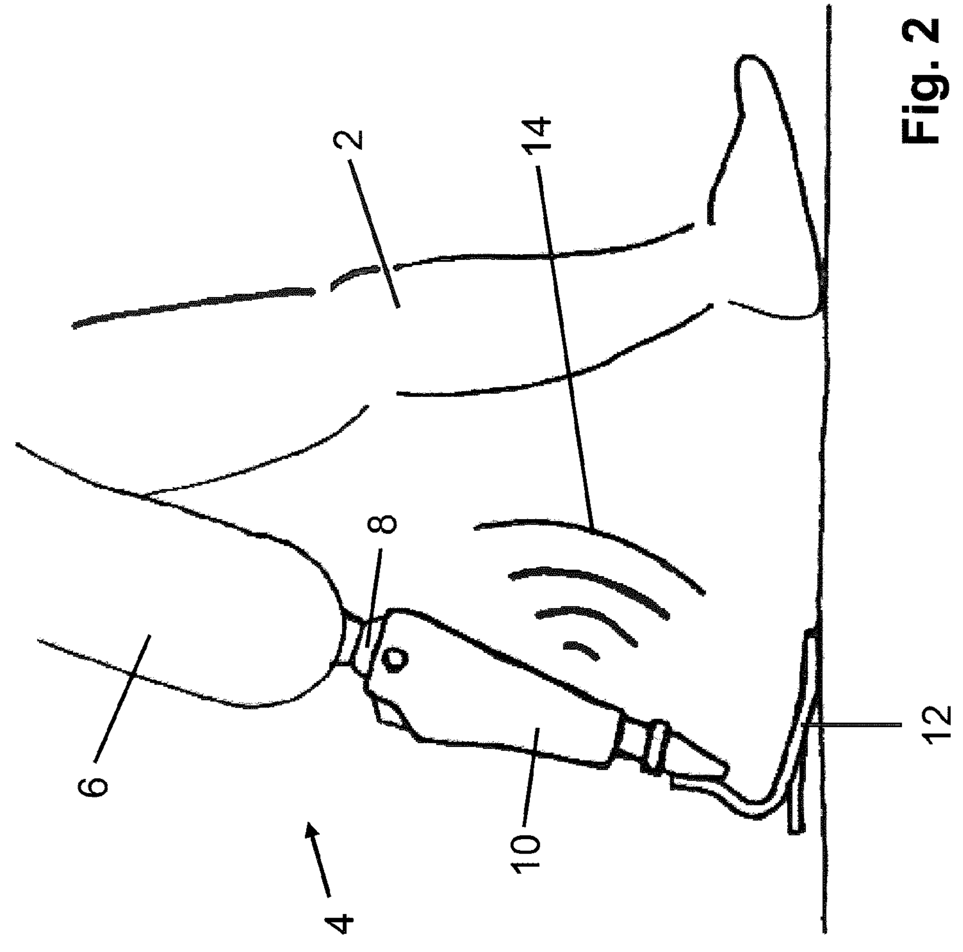
FIG. 2—an orthopedic device worn during walking.

FIG. 2 shows the representation during a step cycle. The contralateral limb 2 is untreated, while an upper leg prosthesis with an upper leg socket 6, knee joint 8, lower leg 10 and foot 12 is located on the ipsilateral limb 4. While the sensors in FIG. 1 have emitted the measuring radiation 14 medially, i.e. almost exclusively to the side, the sensor in FIG. 2 is configured to emit the measuring radiation 14 in the direction of the contralateral limb 2, although it is almost entirely in front of the ipsilateral limb. This can be achieved, for example, by the transmission range into which the sensor emits the measuring radiation 14 being so large that, regardless of the position of the contralateral limb 2, sufficient measuring radiation 14 reaches the contralateral limb 2. Alternatively, the sensor or particularly the transmission device can be rotated or displaced. Alternatively or additionally, the radiation characteristics of the corresponding sensor can be adapted.

Figure 3:
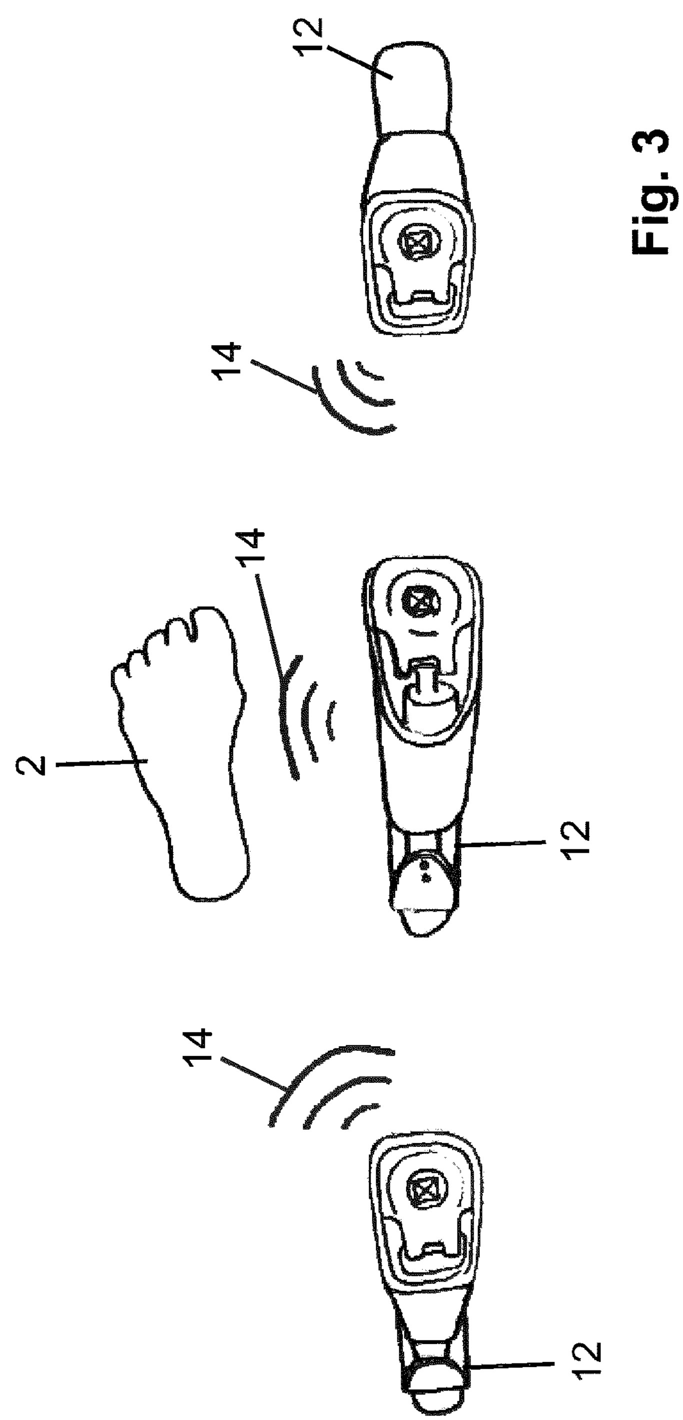
FIG. 3—the orthopedic device from FIG. 1 in a schematic sectional representation in three different step positions, FIG. 4—a schematic representation of an application of a method described here, FIG. 5—a further example of an application, and FIG. 6—a flow diagram.

This is shown in FIG. 3. The foot of the contralateral limb 2 can be recognized as can, in a cropped top view, the foot 12 of the ipsilateral limb 2 in various phases of a step. The ipsilateral limb 4 is performing the swing phase, while the foot of the contralateral limb 2 is securely on the ground. In the far left representation in FIG. 3, the ipsilateral limb has just lost contact with the ground and is beginning the swing phase. The measuring radiation 14 is emitted in a strongly forward direction, as the translateral limb is located in this direction. In the middle of the swing phase, which is shown in the middle of FIG. 3, the ipsilateral limb 4 is directly next to the contralateral limb, so that the measuring radiation 14 is almost completely emitted to the side. At the end of the swing phase, which is shown on the right in FIG. 3, the foot of the ipsilateral limb 4 is located in front of the foot of the contralateral limb 2, so that the measuring radiation 14 is largely emitted backwards.

Figure 4:
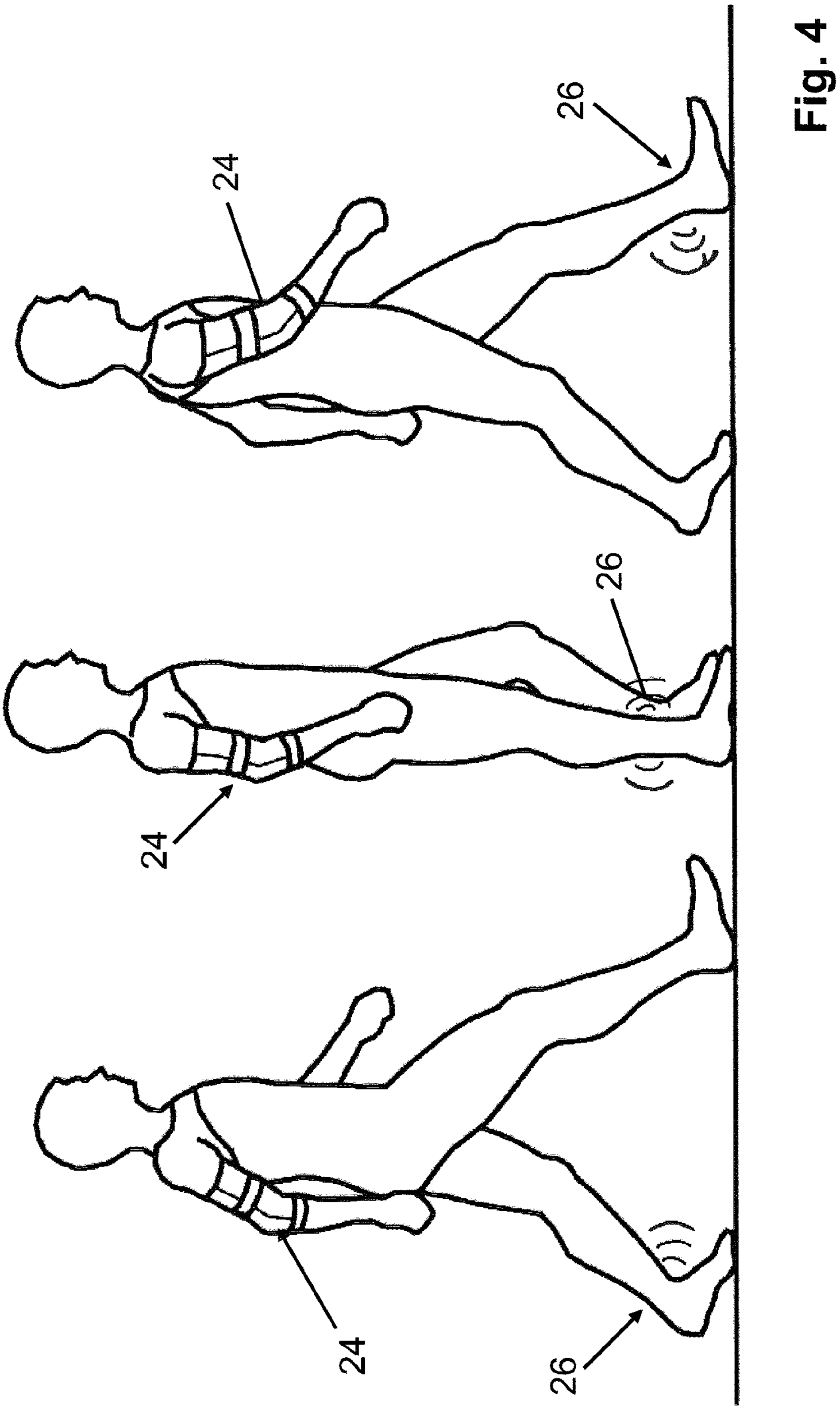

FIG. 4 is an example of the first body part 24, which is the right arm in the example of an embodiment shown, not necessarily having to lie "opposite" the second body part 26, which is the left ankle in the example of an embodiment shown. FIG. 4 shows three positions within a step cycle where in each case the position of the second body part 26, i.e. the left ankle, relative to a further body part, namely the right ankle, is determined. In the left-hand representation in FIG. 4 the second body part 26 is behind the wearer's torso. The same applies for the first body part 24. The relative position of the second body part 26 relative to the right ankle is determined, which is indicated by the three short lines. In the course of the step cycle, the position of the second body part 26 relative to the right ankle changes via the positions shown in the middle of FIG. 4 during the swing phase until it reaches the position shown on the right in FIG. 4 when the heel strikes the ground. Correspondingly, the movement of the first body part 24, which is replaced by an arm prosthesis, is also controlled.

Figure 5:
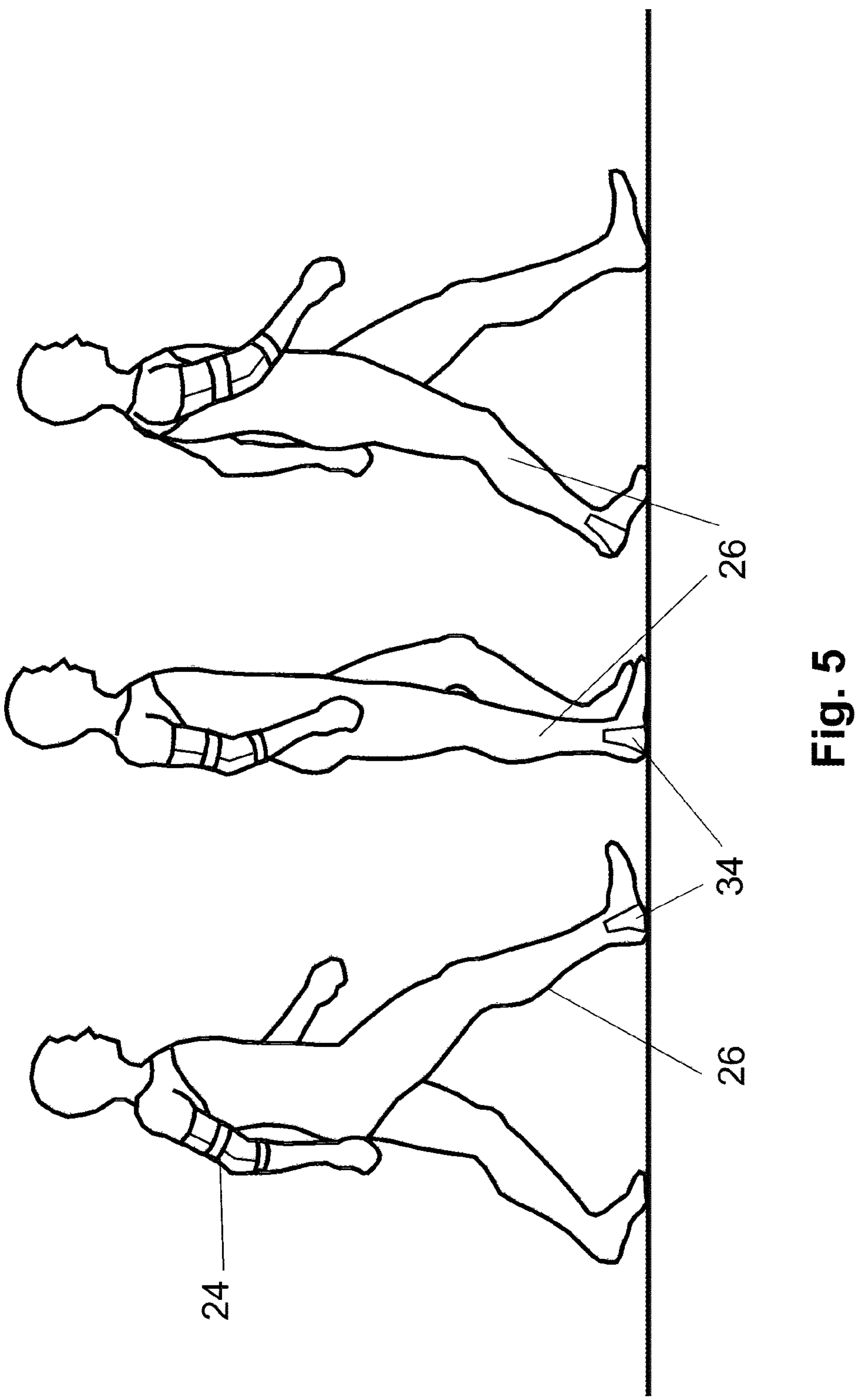

FIG. 5 is an example of the second body part 26, on which a sensor 34 is mounted for determining the movement status, particularly the stance phase in the step cycle, being able to be located on the same half of the body as the body part 24, which is fitted with an orthopedic aid. This sensor can—as in the case of an inertial sensor, for example—obtain information about the movement status solely on the basis of measurements of the limb 26 equipped with the sensor 34. The sensor 34 mounted on the body part 26 can also be used to receive measuring beams that are emitted by the opposite leg or reflected or re-emitted.

Figure 6:
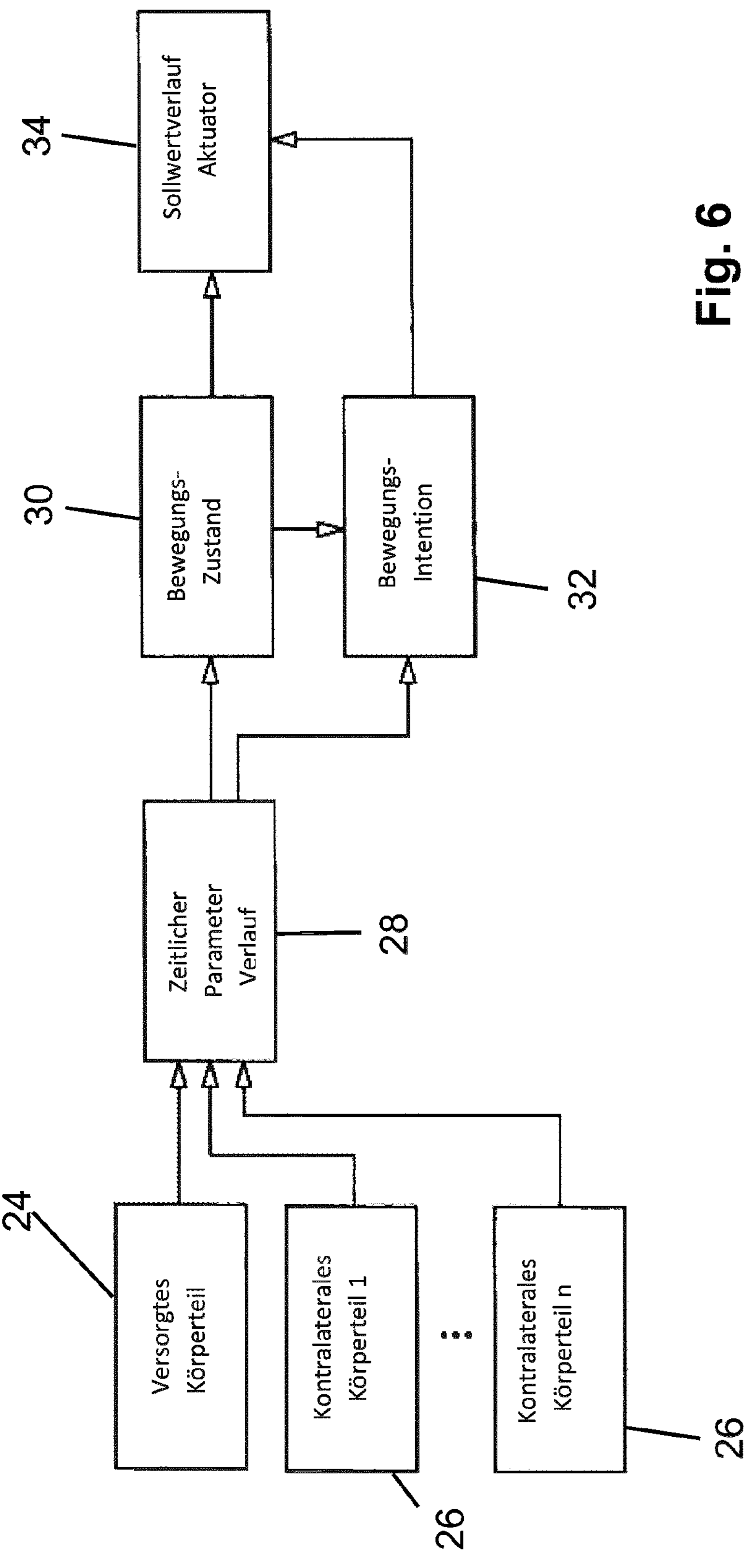

FIG. 6 depicts a schematic flow diagram for a method described here. Parameters are calculated from a first body part 24 and at least a second body part 26; the chronological profile of said parameters is then determined. Both a movement status 30 and movement intention 32 of the wearer are determined from this profile, wherein the determined movement status 30 can also be consulted to determine the movement intention 32. Both the movement intention 32 and the determined movement status 30 can be used separately from each other or in combination to initiate the actuator control unit 34.

REFERENCE LIST 2 contralateral limb
4 ipsilateral limb
6 upper leg socket
8 knee joint
10 lower leg
12 foot

14 measuring radiation
16 lower leg socket
18 upper leg frame
20 lower leg frame
22 knee joint
24 first body part
26 second body part
28 chronological profile
30 movement status
32 movement intention
34 sensor

The invention claimed is:

1. A method for operating an orthopedic device which supports or replaces a first body part of a wearer, and comprises at least one controllable actuator, wherein the method comprises:

a) determining a chronological profile of at least one parameter, which allows for a conclusion to be drawn about a movement status of the wearer, from measurement values of at least one sensor, b) detecting the movement status of the wearer from the at least one determined chronological profile, and c) controlling the at least one controllable actuator depending on the detected movement status of the wearer, wherein at least the chronological profile of at least one parameter of a second body part of the wearer is also used to detect the movement status of the wearer.

2. The method according to claim 1, wherein the second body part does not directly abut the first body part.

3. The method according to claim 1, wherein the at least one parameter is a relative position, relative movement, relative speed, relative acceleration and/or relative angle of the second body part to the first body part and/or of a first part of the second body part to a second part of the second body part.

4. The method according to claim 1, wherein the at least one sensor is configured to detect an absolute angle, a relative angle, a speed, an acceleration, a force, a pressure, a pressure wave, a moment, an electrical field and/or a magnetic field.

5. The method according to claim 1, wherein the first body part is an ipsilateral limb or a part thereof, particularly a foot, an ankle and/or a knee, and the second body part is another limb, preferably a contralateral limb or a part thereof, preferably a foot, an ankle and/or a knee.

6. The method according to claim 1, wherein the at least one sensor is arranged on a component of the orthopedic device or on the first body part and at least also detects measurement values from which the at least one parameter of the second body part is determined.

7. The method according to claim 1, wherein the at least one sensor comprises at least one transmission device and at least one reception device, wherein the transmission device emits measuring radiation, preferably ultrasonic waves and/or electromagnetic measuring radiation, especially preferably radar radiation and/or visible light and/or infrared radiation, and the reception device is configured to receive measuring radiation.

8. The method according to claim 7, wherein the reception device receives measuring radiation reflected or re-emitted by the second body part, and the measurement values and the at least one parameter are determined from a transit time, a phase shift, a frequency shift and/or interference with the emitted measuring radiation.

9. The method according to claim 8, wherein at least one transponder and/or a tag and/or a reflector for the emitted measuring radiation is arranged on the second body part.

10. The method according to claim 1, wherein data of the orthopedic device and/or the wearer is used to determine the at least one parameter, especially to determine the at least one parameter of the second body part.

11. The method according to claim 1, wherein at least one control variable of the at least one controllable actuator is controlled to a set point or a set point profile, which is dependent on the detected movement status and the at least one parameter of the functional body part, preferably the contralateral limb.

12. An orthopedic device for supporting a first body part of a wearer, the orthopedic device comprising:

at least one sensor; and an electric control unit configured to:

determine a chronological profile of at least one parameter, which allows for a conclusion to be drawn about a movement status of the wearer from measurement values from the at least one sensor;

detect the movement status of the wearer from the at least one determined chronological profile; and control the at least one controllable actuator depending on the detected movement status of the wearer; wherein at least the chronological profile of at least one parameter of a second body part of the wearer is also used to detect the movement status of the wearer.

13. The orthopedic device of claim 12, wherein the second body part does not directly abut the first body part.

14. The orthopedic device of claim 12, wherein the at least one parameter is a relative position, relative movement, relative speed, relative acceleration and/or relative angle of the second body part to the first body part and/or of a first part of the second body part to a second part of the second body part.

15. The orthopedic device of claim 12, wherein the at least one sensor is configured to detect an absolute angle, a relative angle, a speed, an acceleration, a force, a pressure, a pressure wave, a moment, an electrical field and/or a magnetic field.

16. The orthopedic device of claim 12, wherein the first body part is an ipsilateral limb or a part thereof, particularly a foot, an ankle and/or a knee, and the second body part is another limb, preferably a contralateral limb or a part thereof, preferably a foot, an ankle and/or a knee.

17. The orthopedic device of claim 12, wherein the at least one sensor is arranged on a component of the orthopedic device or on the first body part and at least also detects measurement values from which the at least one parameter of the second body part is determined.

18. The orthopedic device of claim 12, wherein the at least one sensor comprises at least one transmission device and at least one reception device, wherein the transmission device emits measuring radiation, preferably ultrasonic waves and/or electromagnetic measuring radiation, especially preferably radar radiation and/or visible light and/or infrared radiation, and the reception device is configured to receive measuring radiation.

19. The orthopedic device of claim 18, wherein the reception device receives measuring radiation reflected or re-emitted by the second body part, and the measurement values and the at least one parameter are determined from a transit time, a phase shift, a frequency shift and/or interference with the emitted measuring radiation.

20. A method for operating an orthopedic device which supports or replaces a first body part of a wearer, and comprises at least one controllable actuator, wherein the method comprises:

a) determining at least one chronological profile of at least one parameter, allowing for a conclusion to be drawn about a movement status of the wearer from measurement values of at least one sensor;

b) detecting the movement status of the wearer from the at least one determined chronological profile; and c) controlling the at least one controllable actuator depending on the detected movement status of the wearer;

wherein at least the chronological profile of at least one parameter of a second body part of the wearer is also used to detect the movement status of the wearer, the second body part not directly abutting the first body part; and wherein the first body part is an ipsilateral limb or a part thereof, particularly a foot, an ankle and/or a knee, and the second body part is another limb, preferably a contralateral limb or a part thereof, preferably a foot, an ankle and/or a knee.

* * * * *